(12) United States Patent
Jin et al.

(10) Patent No.: US 11,311,705 B2
(45) Date of Patent: Apr. 26, 2022

(54) MEDICAL PRESSURIZATION CONTROL DEVICE

(71) Applicant: MICRO-TECH (NANJING) CO., LTD., Nanjing (CN)

(72) Inventors: Hongyan Jin, Nanjing (CN); Weiqin Qiu, Nanjing (CN); Changqing Li, Nanjing (CN)

(73) Assignee: MICRO-TECH (NANJING) CO., LTD., Nanjing (CN)

( * ) Notice: Subject to any disclaimer, the term of this patent is extended or adjusted under 35 U.S.C. 154(b) by 318 days.

(21) Appl. No.: 16/497,061

(22) PCT Filed: Mar. 5, 2018

(86) PCT No.: PCT/CN2018/077985
§ 371 (c)(1),
(2) Date: Sep. 24, 2019

(87) PCT Pub. No.: WO2018/177078
PCT Pub. Date: Oct. 4, 2018

(65) Prior Publication Data
US 2020/0376240 A1    Dec. 3, 2020

(30) Foreign Application Priority Data

Mar. 30, 2017 (CN) .......................... 201710200239.7

(51) Int. Cl.
*A61M 29/02* (2006.01)
*A61M 25/10* (2013.01)

(52) U.S. Cl.
CPC ...... *A61M 29/02* (2013.01); *A61M 25/10182* (2013.11); *A61M 2205/3331* (2013.01)

(58) Field of Classification Search
CPC ............ A61M 29/02; A61M 25/10182; A61M 2205/3331

(Continued)

(56) References Cited

U.S. PATENT DOCUMENTS

| 5,931,850 A | 8/1999 | Zadini et al. |
| 2007/0060924 A1* | 3/2007 | Choi .................. A61B 17/8855 606/93 |

FOREIGN PATENT DOCUMENTS

| CN | 201719681 U | 1/2011 |
| CN | 201988040 U | 9/2011 |

(Continued)

*Primary Examiner* — Phillip A Gray
(74) *Attorney, Agent, or Firm* — Tomanage IP

(57) ABSTRACT

The present invention provides a medical pressurization control device, comprising an outer tube and a threaded push rod inside the outer tube. A movable caliper comprising two arms, a caliper control member connected to the movable caliper, and an operating member connected to the caliper control member are provided in the outer tube; when the operating member moves from a second position to a first position, the operating member drives the caliper control member to move to a locking position, so as to push the two arms of the movable caliper to hold the threaded push rod for locking the threaded push rod; when the operating member moves from the first position to the second position, the operating member drives the caliper control member to move to a release position, so as to push the two arms of the movable caliper to release the threaded push rod for unlocking the threaded push rod.

11 Claims, 6 Drawing Sheets

(58) Field of Classification Search
USPC .................................................... 604/97.02
See application file for complete search history.

(56) References Cited

FOREIGN PATENT DOCUMENTS

| | | |
|---|---|---|
| CN | 203183497 U | 9/2013 |
| CN | 203389203 U | 1/2014 |
| CN | 106075705 A | 11/2016 |
| CN | 106237491 A | 12/2016 |
| CN | 106902444 A | 6/2017 |
| CN | 207384590 U | 5/2018 |
| KR | 100550585 B1 | 2/2006 |

\* cited by examiner

MEDICAL PRESSURIZATION CONTROL DEVICE

FIELD OF THE INVENTION

The present invention relates to the field of medical equipment, especially to a medical pressurization control device.

DESCRIPTION OF THE PRIOR ARTS

A medical balloon pressure pump is applicable in a balloon dilation catheter so as to inflate and deflate the balloon, for expansion operations in narrow areas of body cavities. During the expansion, a balloon pressure pump is required to inject liquid and boost pressure into the balloon and to monitor the pressure. In the process of negative pressure suction, it should be convenient for one person to operate in suction and locking up. At present, clinically disposable medical balloon pressure pumps are basically thread-propelled, but differ in thread engagement and unlocking structures, and the typical examples include eccentric type, lever type, lean wedge type and others. Different design structures result in different flaws, but all types need people's hands to realize the thread engagement and unlocking operations. Eccentric ones need another person's help to successfully finish the negative pressure suction operation; lever ones have the risks of malfunction of maintaining the lockup state under negative pressure (i.e., it is impossible to form a stable status of negative pressure). The lean wedge ones require combined efforts of the thumb and the index finger to accomplish negative pressure suction operation. Although this structure is able to successfully finish the movements of releasing, air pumping and locking up without stopping, their capacity is relatively small due to the structure layout, unable to meet the demands of the market for large capacities.

SUMMARY OF THE INVENTION

The purpose of the present invention: the present invention aims to overcome the shortcomings of the prior arts, and to provide a medical pressurization control device.

In order to overcome the abovementioned problems, the present invention provides a medical pressurization control device comprising an outer tube and a threaded push rod located in the outer tube; wherein the outer tube comprises a movable caliper with two arms, a caliper control member connected with the movable caliper; and an operating member connected with the caliper control member;

when said operating member moves from a second position to a first position, the operating member drives the caliper control member to a locked position, and then the two arms of the movable caliper are pushed to firmly hold the threaded push rod so as to lock the threaded push rod;

when said operating member moves from the first position to the second position, said operating member drives the caliper control member to a release position, and then the two arms of the movable caliper are pushed to loosen their holding on the threaded push rod so as to release the threaded push rod.

In the present invention, the two arms of the movable caliper are respectively a first locknut arm and a second locknut arm, one end respectively of the first locknut arm and of the second locknut arm is connected to each other mutually through a pin, or is fixed onto two pins respectively; the first locknut arm and the second locknut arm hold the threaded push rod from two sides separately.

In the present invention, the inner sides of the first locknut arm and the second locknut arm have threads that match that of the threaded push rod, and therefore, when they firmly hold the threaded push rod, they lock up the threaded push rod in position.

In the present invention, the caliper control member is a movable piece, such movable piece includes a first fastening side, a middle unlocking unit and a second fastening side, the middle unlocking unit includes a protrusion that matches the two inner walls of the first locknut arm and the second locknut arm; when the movable piece moves outwards, the protrusion opens the first locknut arm and the second locknut arm towards outside, and the first fastening side and the second fastening side match the two outer walls of the first locknut arm and the second locknut arm; when the movable piece moves inward, the first fastening side and the second fastening side press inwardly the first locknut arm and the second locknut arm, and then the first locknut arm and the second locknut arm are driven to tightly fasten the threaded push rod in position.

In the present invention, the width of the outermost side of the protrusion is larger than that of its inner side, which makes it possible for the outward movement of the protrusion to open the first locknut arm and the second locknut arm.

In the present invention, the operating member includes a lever, the lever includes a head connecting end, a middle support end and a tail operational end; the head connecting end is connected to the movable piece, the middle support end is pivotally mounted on the outer tube, and a press on the tail operational end drives the head connecting end to move the movable piece toward outside through lever action.

In the present invention, the middle support end of the lever has a torsional spring, the torsional spring connects to the outer tube through a pin, and loosening the press on the tail operational end enables the head connecting end to automatically drive the movable piece to move inward through lever action.

In the present invention, the outer walls of the first locknut arm and the second locknut arm are curved structures, the outer wall radians of the first locknut arm and the second locknut arm respectively match the first fastening side and the second fastening side, and when the first fastening side and the second fastening side move inwards, the first locknut arm and the second locknut arm are pressed inwards to tightly enclasp the threaded push rod in position.

In the present invention, the inner walls of the first locknut arm and the second locknut arm are curved structures, the inner wall radians of the first locknut arm and the second locknut arm respectively match the protrusion, and when the protrusion moves outwards, it is able to open the first locknut arm and the second locknut arm to a position that no influence is exerted to the movement of the threaded push rod.

In the present invention, the caliper control member is a movable piece, said movable piece includes a first fastening side and a second fastening side;

the first fastening side and the second fastening side match the two outer walls of the first locknut arm and the second locknut arm; when the movable piece moves inward, the first fastening side and the second fastening side press inwardly the first locknut arm and the second locknut arm, and then the first locknut arm and the second locknut arm are able to tightly enclasp the threaded push rod in position.

Merits: the present invention takes advantages of lever action to realize the operation of negative pressure suction by releasing the locknut with just one finger, and its structure is convenient and quick for operation. Furthermore, the pressure maintenance performance after locking is stable. The special structures of the movable piece and the locknut arms with the action of the lever make it effective for any detaching and locking operations.

BRIEF DESCRIPTION OF THE DRAWINGS

The following drawings together with embodiments will help further explain the present invention, and make its merits much clearer.

DETAILED DESCRIPTION OF THE PREFERRED EMBODIMENTS

The following is a detailed explanation of the present invention with the aid of FIG. 1 to FIG. 9.

Embodiment 1

The embodiment discloses a medical pressurization control device comprising an outer tube 14 and a threaded push rod 1 located in the outer tube 14 and the outer tube 14 comprises a movable caliper with two arms, a caliper control member connected with the movable caliper, and the device further comprises an operating member connected with the caliper control member; the operating member is able to move between a first position and a second position;

When said operating member moves from the second position to the first position, the operating member drives the caliper control member to move to a locking position, and the two arms of the movable caliper are correspondingly driven to firmly hold the threaded push rod 1 so as to lock the threaded push rod 1.

When said operating member moves from the first position to the second position, the operating member drives the caliper control member to move to a release position, and the two arms of the movable caliper are correspondingly compelled to lose their holding on the threaded push rod 1 so as to release the threaded push rod 1.

The two arms of the movable caliper are respectively a first locknut arm 2 and a second locknut arm 4, one end respectively of the first locknut arm and the second locknut arm is connected to each other mutually through a pin, and the first locknut arm 2 and the second locknut arm 4 hold the threaded push rod 1 from two sides separately.

Figure 5:
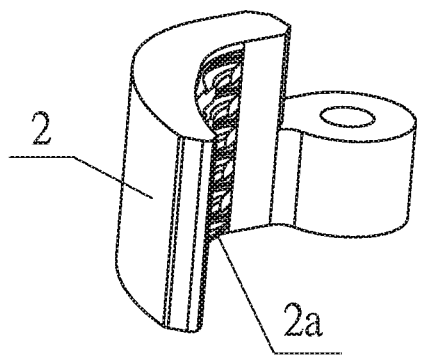
FIG. 5 is a schematic view of the first locknut arm.
Figure 6:
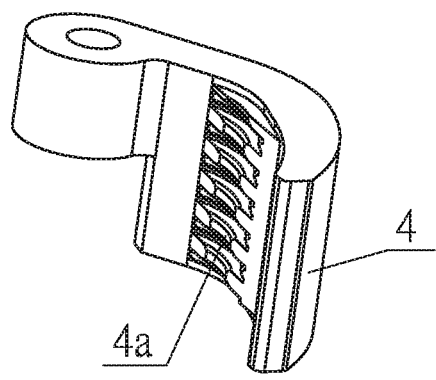
FIG. 6 is a schematic view of the second locknut arm.

As shown in FIG. 5 and FIG. 6, the inner sides of the first locknut arm 2 and the second locknut arm 4 have thread 2a and thread 4a that match that of the threaded push rod 1. Therefore, when the first locknut arm 2 and the second locknut arm 4 firmly hold the threaded push rod 1, they lock the threaded push rod 1 in position.

Figure 4:
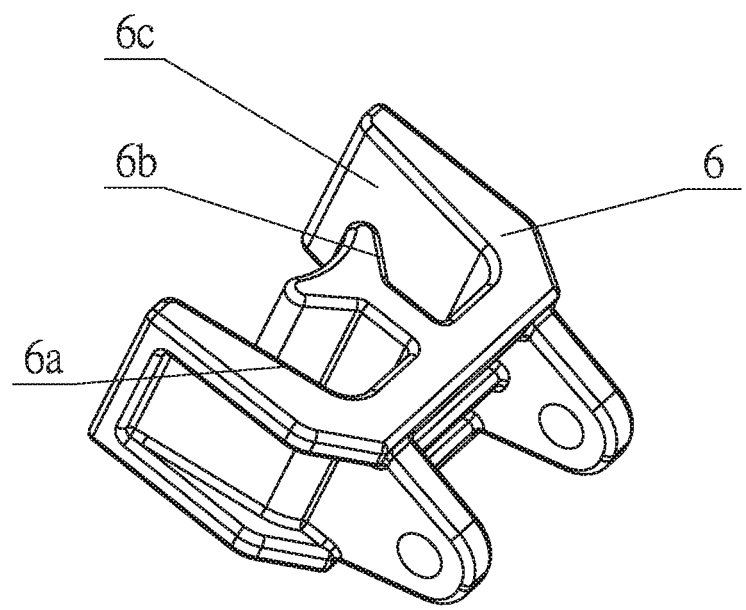
FIG. 4 is a schematic view of the movable piece.

As shown in FIG. 4, the caliper control member is a movable piece 6, and the movable piece 6 includes a first fastening side 6a, a middle unlocking unit 6b and a second fastening side 6c; the middle unlocking unit 6b includes a protrusion that matches the two inner walls of the first locknut arm 2 and the second locknut arm 4. When the movable piece 6 moves outwards, the protrusion of the middle unlocking unit 6b opens the first locknut arm 2 and the second locknut arm 4 towards outside, and the first fastening side 6a and the second fastening side 6c match the two outer walls of the first locknut arm 2 and the second locknut arm 4. When the movable piece 6 moves inward, the first fastening side 6a and the second fastening side 6c press inwardly the first locknut arm 2 and the second locknut arm 4, and the first locknut arm 2 and the second locknut arm 4 will be forced to tightly enclasp the threaded push rod 1 in position.

The width of the outermost side of the middle unlocking unit 6b's protrusion is larger than that of its inner side, enabling the outward movement of the protrusion of the middle unlocking unit 6b to open the first locknut arm 2 and the second locknut arm 4.

The operating member includes a lever 8. The lever 8 includes a head connecting end, a middle support end and a tail operational end. The head connecting end connects to the movable piece 6. The middle support end is pivotally mounted on the outer tube 14. Pressing the tail operational end drives the head connecting end to move the movable piece 6 towards outside through lever action.

The middle support end of the lever 8 has a torsional spring 10. The torsional spring 10 connects to the outer tube 14 through a middle pin 9. Loosening the tail operational end enables the head connecting end to automatically drive the movable piece 6 to move inward with the action of the torsional spring 10.

The outer walls of the first locknut arm 2 and the second locknut arm 4 are curved structures. The radians of the outer walls of the first locknut arm 2 and the second locknut arm 4 respectively match the first fastening side 6a and the second fastening side 6c. That makes it possible for the inward movement of the first fastening side 6a and the second fastening side 6c to press the first locknut arm 2 and the second locknut arm 4 inwards so as to tightly enclasp the threaded push rod 1 in position.

The inner walls of the first locknut arm 2 and the second locknut arm 4 are curved structures, and the radians of the inner walls of the first locknut arm 2 and the second locknut arm 4 respectively match the middle unlocking unit 6b's protrusion. When the protrusion of the middle unlocking unit 6b moves outwards, it is able to open the first locknut arm 2 and the second locknut arm 4 to a position that no influence is exerted to the movement of the threaded push rod 1.

The Structures and Implementation Steps of Embodiment 1

As shown in FIG. 1, FIG. 2a, FIG. 2b and FIG. 3, the embodiment provides a medical pressurization control device comprising a threaded push rod 1, a first locknut arm 2, a pin 3, a second locknut arm 4, a fixing base 5, a movable piece 6, a head pin 7, a lever 8, a middle pin 9, a torsional spring 10, a piston base 11, an O-type ring 12, a piston cap 13, an outer tube 14, a pressure gauge 15, a connector 16 and a mesh tube 17. The pin 3 is used to connect the first locknut arm 2 and the second locknut arm 4. The head pin 7 is used to connect the movable piece 6 and the lever 8. The middle pin 9 is used to connect the torsional spring 10 and the lever 8. Lastly, the pin 3 connected with said components is mounted on the fixing base 5. The threaded push rod 1, the fixing base 5, the piston base 11, the O-type ring 12 and the piston cap 13 are assembled before being put into the outer tube 14 in sequence. The head pin 7 and the middle pin 9 connected with components are mounted on the fixing base 5 and the outer tube 14 in sequence. In the end, the pressure gauge 15 is cemented onto the outer tube 14, and the connector 16 and the mesh tube 17 shall be glued together before they are pasted onto the outer tube 14 to finish the assembly of the disposable medical balloon pressure pump.

Figure 1:
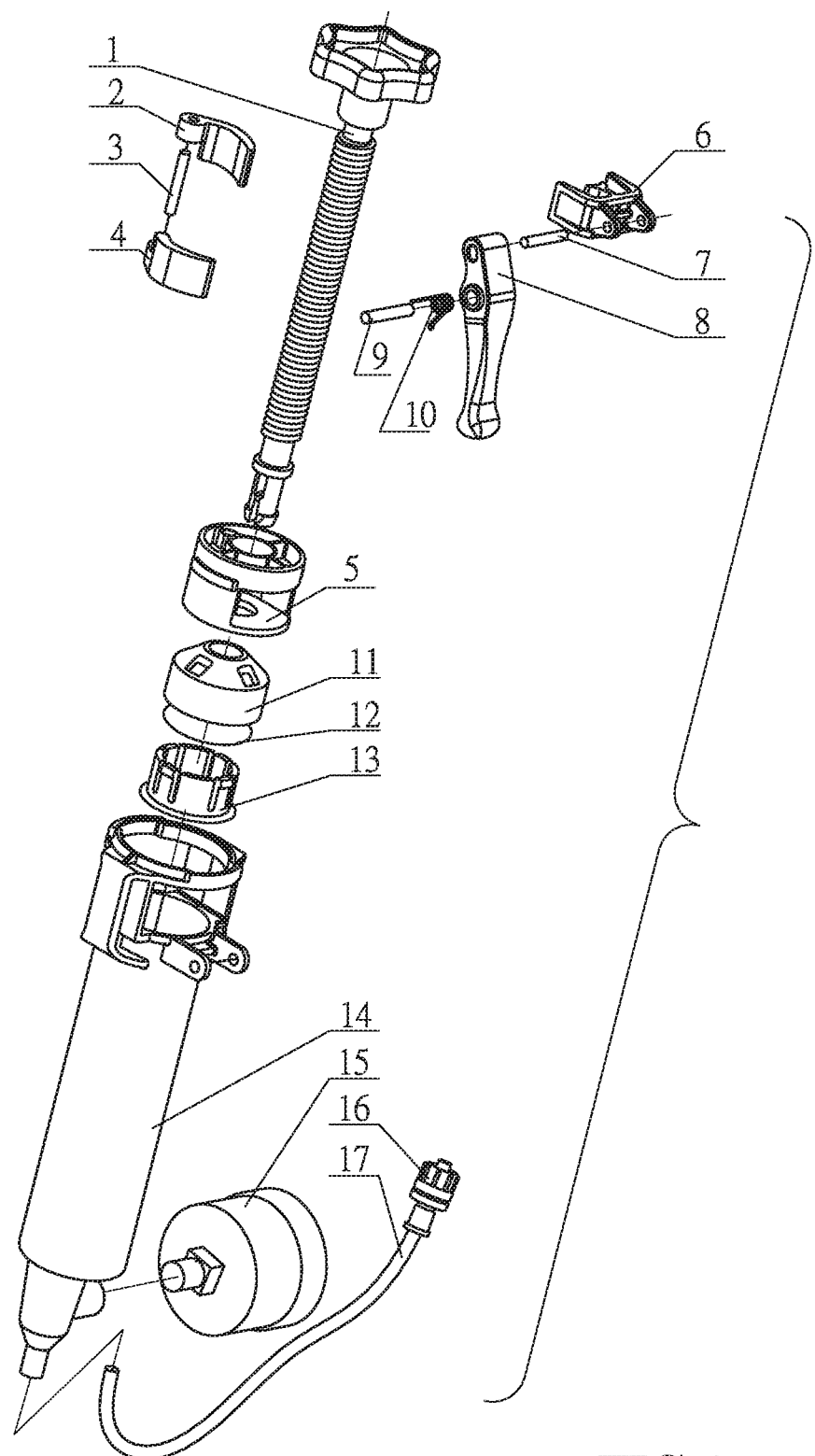
FIG. 1 is an exploded view of the medical pressurization control device.
Figure 2A:
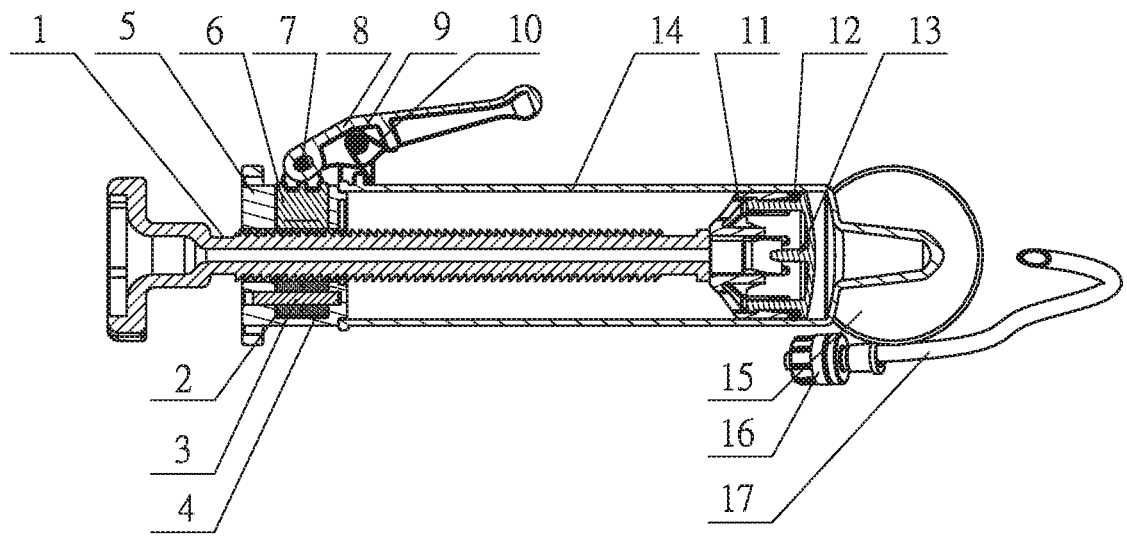
FIG. 2a is a sectional view of the medical pressurization control device in a locked state.
Figure 2B:
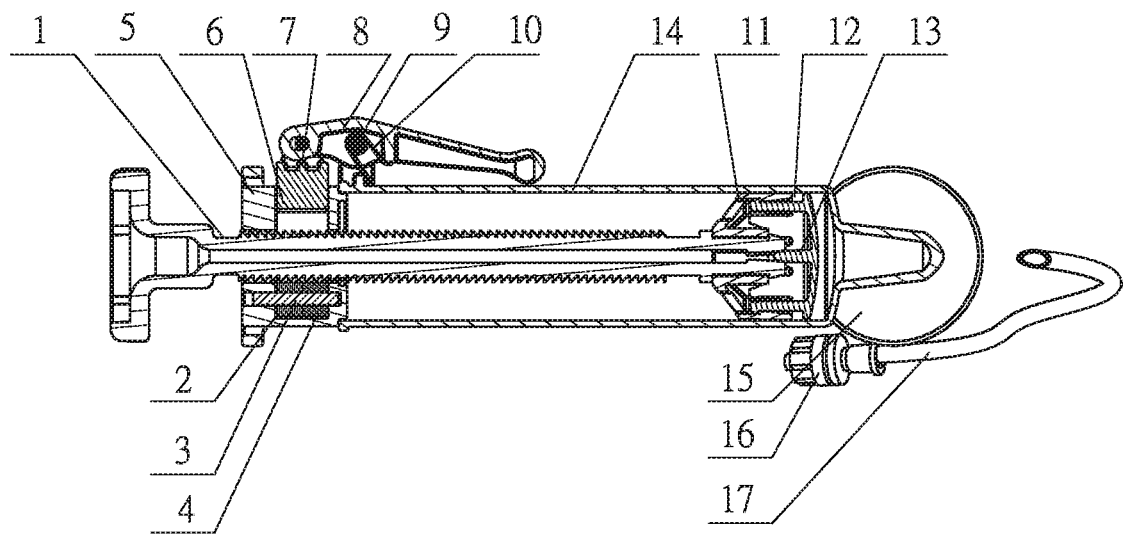
FIG. 2b is a sectional view of the medical pressurization control device in an unlocked state.
Figure 3:
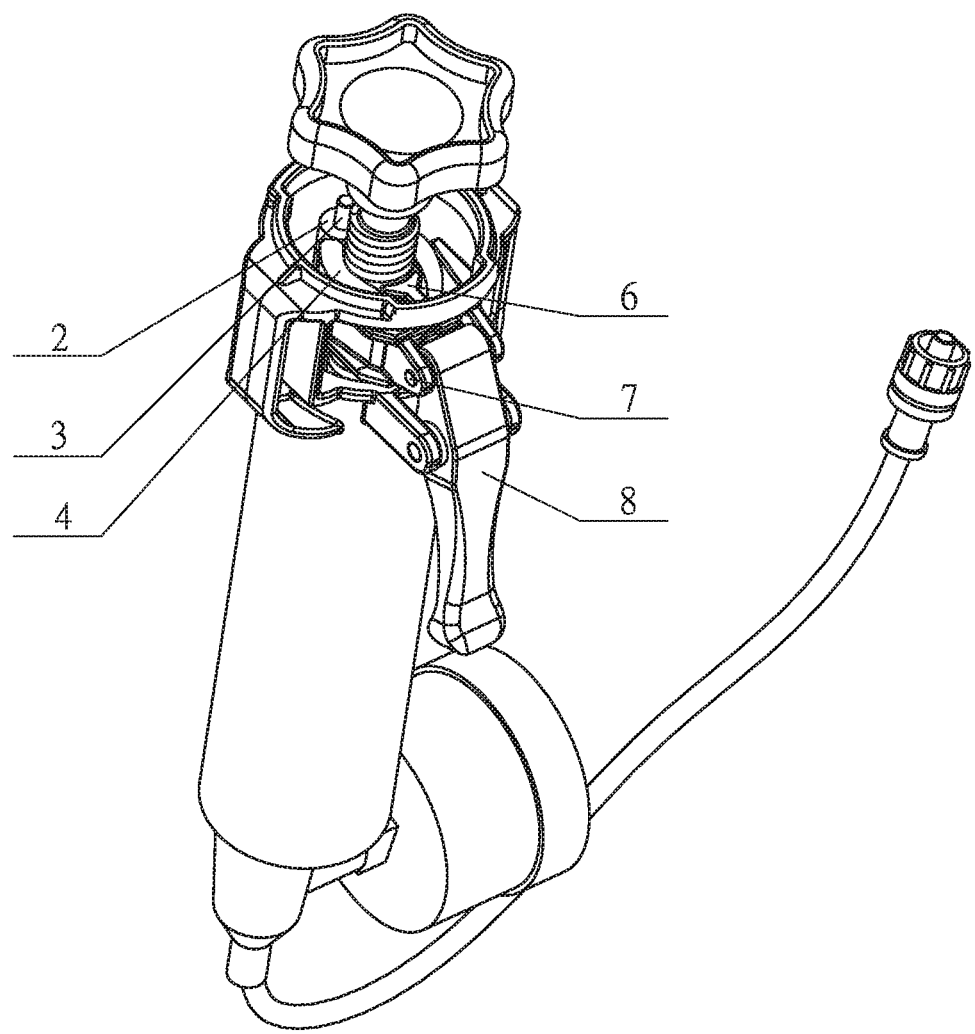
FIG. 3 is a schematic view of the medical pressurization control device.

As shown in FIG. 2a, FIG. 2b and FIG. 4, the movable piece 6 comprises the first fastening side 6a, the middle unlocking unit 6b and the second fastening side 6c. When the tail of the lever 8 is pressed, the outward movement of the head of the lever 8 drives the middle unlocking unit 6b of the movable piece 6 to open the first locknut arm 2 and the second locknut arm 4; as a result, the lever 8 is moved to the second position. When the lever 8's tail is released, with the action of the torsional spring 10, the first fastening side 6a and the second fastening side 6c respectively press inwards the first locknut arm 2 and the second locknut arm 4, and the lever 8 is compelled to return to the first position.

Figure 7:
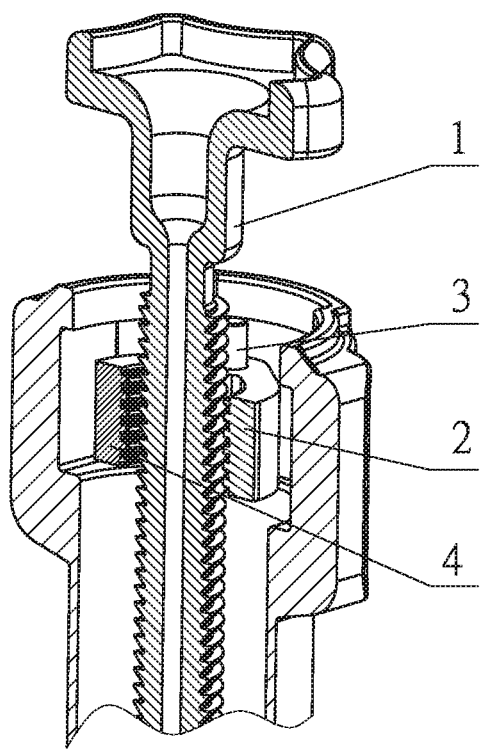
FIG. 7 is a schematic view of one embodiment in an engaged state.
Figure 8:
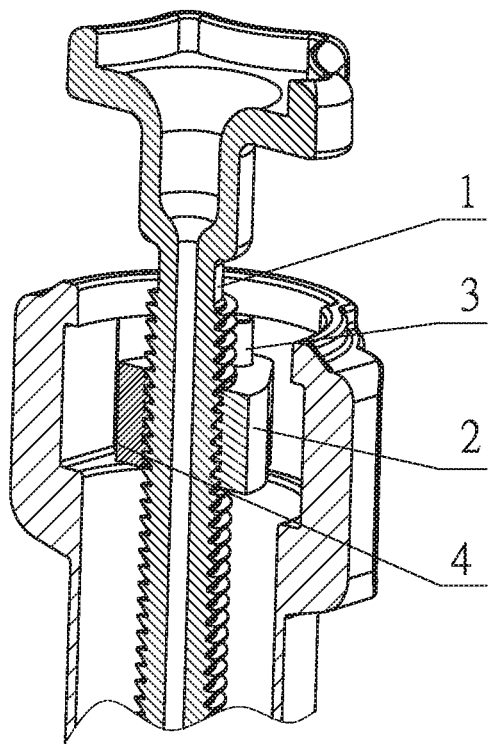
FIG. 8 is a schematic view of one embodiment in an unlocked state.

As shown in FIG. 5 and FIG. 6, the first locknut arm 2 and the second locknut arm 4 respectively have the first thread 2a and the second thread 4a that match that of the threaded push rod. As shown in FIG. 7, when the lever 8 is on the first position, the first locknut arm and the second locknut arm are capable of tightly locking up the threaded push rod. As shown in FIG. 8, when the lever 8 is on the second position, the depths of the first thread 2a and the second thread 4a are unable to prevent the radial movement of the threaded push rod.

When the embodiment is in the working state, in the initial position the action of the torsional spring 10 makes the first locknut arm 2 and the second locknut arm 4 in the tightly-locked condition, which realizes the aim of limiting the location of the threaded push rod with the two arms of the movable caliper. In such a condition, rotating the threaded push rod 1 is able to increase pressure of the liquid injected balloon to realize expansion operations.

As shown in FIGS. 2a and 2b, in the operations of fast liquid injection, liquid pumping or negative pressure suction, the little finger and the ring finger of the left hand are able to press the lever 8 to overcome the twisting force of torsional spring 10, and the middle unlocking unit 6b of the movable piece 6 is driven to open up the first locknut arm 2 and the second locknut arm 4. Then the engagement of the first thread 2a and the second tread 4a with the threaded push rod 1 is changed into an unlocked state, releasing the threaded push rod 1 from being bound. It should be explained that after the operation of negative pressure suction, the fingers used for releasing should be relaxed so that the locknut arm 2 and the locknut arm 4 are engaged with the threaded push rod 1 to perform the role of maintaining pressure.

In the embodiment, a release from the engagement of the first locknut arm 2 and the second locknut arm 4 is carried out for operations including liquid injection, liquid pumping or negative pressure suction as well as pressure maintenance, all of which could be implemented without stopping, a convenient operation.

The present invention reasonably takes advantages of the lever principle, adopting the middle pin 9 of the outer tube 14 as the point of support and the torsional spring 10 for stabilization. In addition, the movable piece 6 has a special structure which makes the threaded push rod 1 with the action of the lever effectively engaged with the locknut arm 2 and the locknut arm 4 and released from such engagement.

The head part of the movable piece 6 is similar to an E structure overall, including the first fastening side 6a, the middle unlocking unit 6b and the second fastening side 6c. The movable piece 6 can effectively control the engagement and detachment between the locknut arm 2 and the locknut arm 4 and the threaded push rod 1. The middle unlocking unit 6b of the movable piece 6 is a Y type core. The Y type core is driven by lever force to move outwards, then the two "crescent" left and right locknut arms, i.e. the first locknut arm 2 and the second locknut arm 4 around the pin 3 are forced to move outwards so as to realize the purpose of detaching the threaded push rod 1 from being grasped. When the lever 8 is released, the force of the torsional spring 10 drives the first fastening side 6a and the second fastening side 6c of the movable piece 6 to furl the crescent left and right locknut arms inwards at the same time to hold the pin 3. That enables the left and right locknut arms to firmly hold the threaded push rod 1 and to maintain the effective locking state of the left and right locknut arms around the threaded push rod.

The first thread 2a of the first locknut arm 2 and the second thread 4a of the second locknut arm 4 can match the thread structure of the threaded push rod 1. The two inner walls of the first fastening side 6a and the second fastening side 6c of the E structure movable piece have a firm hold on the curved outer walls of the first locknut arm 2 and the second locknut arm 4, which is the key to ensure the effective locking with threads. Such structure can effectively ensure the durable locking of the threads without occurrence of malfunction during corresponding operations of the pressure pump, especially the operation of pressure maintenance.

Embodiment 2

Figure 9:
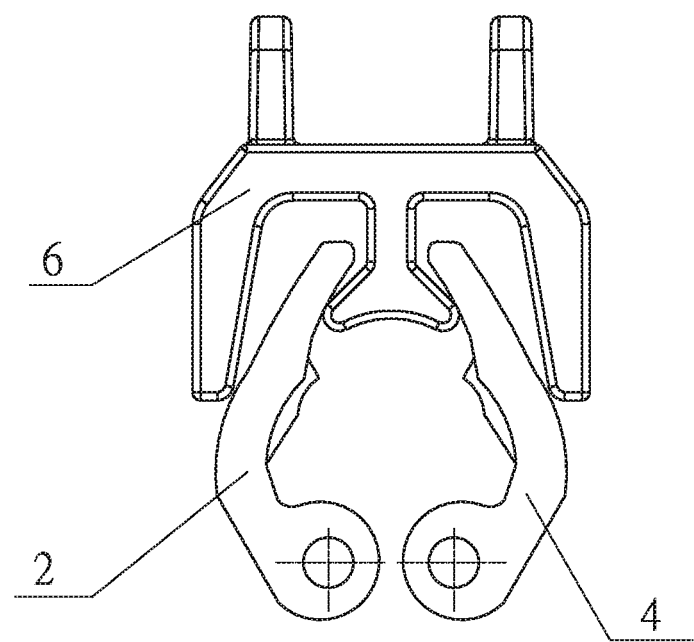
FIG. 9 is a schematic view of two locknut arms around the two pins.

As shown in FIG. 9, either the first locknut arm 2 or the second locknut arm 4 connects the fixing base through a pin, respectively.

The present invention provides a medical pressurization control device, there are lots of methods and ways to realize the technical solution, the abovementioned embodiments are only preferable ones of the present invention, and it should be pointed out that, for a skilled person in the field, under the invention principle of the present invention, any possible changes and modifications made on the technical solution shall be regarded within the claimed ranges of the present invention. The undefined parts comprised in the embodiments are all able to be realized with prior arts.

What is claimed is:

1. A medical pressurization control device comprising an outer tube, a threaded push rod located in the outer tube, and an operating member, characterized in that the outer tube comprises a movable caliper with two arms, a caliper control member connected with the movable caliper, and the operating member is connected with the caliper control member; the operating member is able to move between a first position and a second position;

when said operating member moves from the second position to the first position, the operating member drives the caliper control member to a locking position, and then the two arms of the movable caliper are pushed to firmly hold the threaded push rod so as to lock the threaded push rod;

when said operating member moves from the first position to the second position, said operating member drives the caliper control member to a release position, and then the two arms of the movable caliper are pushed to loosen their holding on the threaded push rod so as to release the threaded push rod.

2. The medical pressurization control device as claimed in claim 1, characterized in that the two arms of the movable caliper are respectively a first locknut arm and a second locknut arm, the first locknut arm connects with the second locknut arm mutually through a pin, and the first locknut arm and the second locknut arm hold the threaded push rod from two sides of the threaded push rod separately.

3. The medical pressurization control device as claimed in claim 2, characterized in that the inner sides of the first locknut arm and the second locknut arm have threads that match that of the threaded push rod, such that when the first locknut arm and the second locknut arm firmly hold the threaded push rod, they lock the threaded push rod in position.

4. The medical pressurization control device as claimed in claim 2, characterized in that the caliper control member is a movable piece, said movable piece includes a first fastening side, a middle unlocking unit and a second fastening side, and the middle unlocking unit includes a protrusion that matches the two inner walls of the first locknut arm and the second locknut arm; when the movable piece moves outward, the protrusion opens the first locknut arm and the second locknut arm towards outside; the first fastening side and the second fastening side match the two outer walls of the first locknut arm and the second locknut arm; when the movable piece moves inward, the first fastening side and the second fastening side press inwardly the first locknut arm and the second locknut arm, and then the first locknut arm and the second locknut arm are able to tightly enclasp the threaded push rod in position.

5. The medical pressurization control device as claimed in claim 4, characterized in that the width of the outermost side of the protrusion is larger than that of its inner side, which makes it possible for the outward movement of the protrusion to open up the first locknut arm and the second locknut arm.

6. The medical pressurization control device as claimed in claim 4, characterized in that the operating member includes a lever, the lever includes a head connecting end, a middle support end and a tail operational end, the head connecting end is connected to the movable piece, the middle support end is pivotally mounted on the outer tube; a press on the tail operational end drives the head connecting end to move the movable piece towards outside through lever action.

7. The medical pressurization control device as claimed in claim 5, characterized in that the middle support end of the lever has a torsional spring, the torsional spring connects to the outer tube through a middle pin; loosening the press on the tail operational end enables the head connecting end to automatically drive the movable piece to move inward with the action of the torsional spring.

8. The medical pressurization control device as claimed in claim 4, characterized in that the outer walls of the first locknut arm and the second locknut arm are curved structures, the outer wall radians of the first locknut arm and the second locknut arm respectively match the first fastening side and the second fastening side; when the first fastening side and the second fastening side move inwards, the first locknut arm and the second locknut arm are pressed inwards to tightly enclasp the threaded push rod in position.

9. The medical pressurization control device as claimed in claim 4, characterized in that the inner walls of the first locknut arm and the second locknut arm are curved structures, the outer inner wall radians of the first locknut arm and the second locknut arm respectively match the protrusion; when the protrusion moves outwards, it is able to open the first locknut arm and the second locknut arm to a position that no influence is exerted to the movement of the threaded push rod.

10. The medical pressurization control device as claimed in claim 1, characterized in that the two arms of the movable caliper are respectively a first locknut arm and a second locknut arm; either the first locknut arm or the second locknut arm connects with the other through a pin and respectively holds the threaded push rod from two sides of the threaded push rod separately.

11. The medical pressurization control device as claimed in claim 2, characterized in that the caliper control member is a movable piece, said movable piece includes a first fastening side and a second fastening side;

the first fastening side and the second fastening side match the two outer walls of the first locknut arm and the second locknut arm; when the movable piece moves inward, the first fastening side and the second fastening side press inwardly the first locknut arm and the second locknut arm, and then the first locknut arm and the second locknut arm are able to tightly enclasp the threaded push rod in position.

* * * * *